(12) United States Patent
Schneider (10) Patent No.: US 8,910,689 B2
(45) Date of Patent: Dec. 16, 2014

(54) APPARATUS FOR REDUCING DOWNTIME IN WEB PROCESSES

(75) Inventor: Uwe Schneider, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 2152 days.

(21) Appl. No.: 11/079,963

(22) Filed: Mar. 15, 2005

(65) Prior Publication Data

US 2006/0207716 A1 Sep. 21, 2006

(51) Int. Cl.
*B65H 19/00* (2006.01)
*B65H 26/02* (2006.01)
*B65H 21/00* (2006.01)
*B65H 20/24* (2006.01)

(52) U.S. Cl.
CPC ............... *B65H 21/00* (2013.01); *B65H 26/02* (2013.01); *B65H 2301/515* (2013.01); *B65H 2511/52* (2013.01); *B65H 20/24* (2013.01)
USPC .......................................... 156/504; 156/506

(58) Field of Classification Search
USPC .................. 156/504, 506, 507, 64, 251, 515; 242/554.5, 555, 555.1, 555.2, 555.4
See application file for complete search history.

(56) References Cited

U.S. PATENT DOCUMENTS

| 3,822,838 | A |   | 7/1974 | Butler, Jr. et al. |
|---|---|---|---|---|
| 3,836,089 | A |   | 9/1974 | Riemersma |
| 4,165,842 | A | * | 8/1979 | Mengel ....................... 242/554.2 |
| 4,404,052 | A |   | 9/1983 | Persson et al. |
| 4,460,430 | A |   | 7/1984 | Kissell et al. |
| 4,531,999 | A |   | 7/1985 | Persson et al. |
| 4,566,654 | A | * | 1/1986 | Maetani ...................... 242/333.1 |
| 4,566,922 | A | * | 1/1986 | Martinez ......................... 156/64 |
| 4,704,180 | A |   | 11/1987 | Marsella et al. |
| 4,899,691 | A |   | 2/1990 | Fitzgerald, Jr. et al. |
| 5,320,698 | A |   | 6/1994 | Fournier et al. |
| 5,514,237 | A | * | 5/1996 | Emenaker et al. ............. 156/159 |
| 5,671,895 | A |   | 9/1997 | Cederholm et al. |
| 5,707,024 | A | * | 1/1998 | Mellquist et al. .......... 242/418.1 |
| 5,813,587 | A |   | 9/1998 | Nordgren |

(Continued)

FOREIGN PATENT DOCUMENTS

| DE | 4312534 A1 | 1/1995 |
|---|---|---|
| DE | 102 34 912 A1 | 2/2003 |

(Continued)

OTHER PUBLICATIONS

PCT International Search Report.

*Primary Examiner* — Henry Yuen
*Assistant Examiner* — Ayub Maye
(74) *Attorney, Agent, or Firm* — Charles R. Matson; Laura L. Whitmer; George H. Leal (57) ABSTRACT

An apparatus for reducing downtime in processes utilizing continuous webs as a raw material upon the detection of a defective portion in a continuous web includes a defect detection member. The defect detection member detects the defects in the continuous web while a first engaging member can stop or slow the speed of the continuous web upon the detection of the defective portion. A second engaging member can receive the defective portion and separate the defective portion from the continuous web and can attach non-defective portions together. A storage element can provide a contingent amount of the continuous web to any downstream processes while the continuous web is stopped or slowed by the first engaging member.

10 Claims, 8 Drawing Sheets

(56) References Cited

U.S. PATENT DOCUMENTS

| | | | |
|---|---|---|---|
| 5,913,991 A * | 6/1999 | Kubota et al. | 156/64 |
| 6,627,023 B1 | 9/2003 | Gleichenhagen et al. | |
| 6,849,851 B2 * | 2/2005 | Komulainen et al. | 250/340 |
| 6,856,850 B2 | 2/2005 | Rajala et al. | |
| 6,863,945 B2 | 3/2005 | Beitz et al. | |
| 2002/0141712 A1 | 10/2002 | O'Conner et al. | |
| 2002/0146524 A1 | 10/2002 | Ulbrich et al. | |
| 2004/0072664 A1 | 4/2004 | Spatafora et al. | |
| 2004/0074590 A1 | 4/2004 | Canti et al. | |
| 2004/0089398 A1 | 5/2004 | Ulbrich et al. | |
| 2004/0238105 A1 | 12/2004 | Schneider et al. | |

FOREIGN PATENT DOCUMENTS

| | | |
|---|---|---|
| EP | 1 279 384 A1 | 1/2003 |
| EP | 1 184 311 B1 | 10/2004 |
| JP | 58021507 | 2/1983 |

* cited by examiner

APPARATUS FOR REDUCING DOWNTIME IN WEB PROCESSES

FIELD OF THE INVENTION

The present invention relates to an apparatus for reducing downtime in processes utilizing continuous webs. Specifically, the apparatus of the present invention reduces the downtime experienced by a production line when a defective portion of the continuous web is detected. Moreover, the apparatus of the present invention reduces the number of finished products affected by the defective portion.

BACKGROUND OF THE INVENTION

Due to their widespread use, absorbent articles are often produced on high speed production lines. These production lines often include many different processes or stages. These stages are often linked together to increase overall manufacturing efficiency. In general, the stages utilize continuous webs of fabrics, films, foams, elastomerics, etc., in order to create an absorbent article. However, defects in the continuous web can cause significant problems in the production line.

Defects in a continuous web can cause equipment downtime. A defective portion of a continuous web can be removed before the defective portion of the web is further processed in a downstream stage. However, in order to remove the defective portion of the continuous web, the entire production line often may have to be shut down. Unfortunately, the shutting down of the production line can cause a significant loss of production time.

Another ramification of shutting down the production line is that operating personnel may need to be adjusted to insure a smooth startup. For example, equipment in a particular stage may require a lengthy startup period. In general, equipment in upstream or downstream stages cannot begin processing the continuous web until the startup period for the process equipment in the particular stage is completed. The monitoring of equipment in various stages to ensure smooth startup of the production line may require more operating personnel or may require shifting existing operating personnel. The addition of operating personnel can be costly, and shifting existing operating personnel from other areas may cause problems in the areas left unattended. Thus, the shutting down of a stage or multiple stages can be costly to a manufacturer.

Alternatively, the defective portion may be processed instead of removed. However, if the defective portion is not removed, then a number of finished products, e.g. absorbent articles, may be impacted. In general, the absorbent articles containing a part of the defective portion of the continuous web are disposed of because of the defect. The number of absorbent articles affected by the defective portion, which subsequently must be disposed of, can be quite large if the defective portion of the continuous web spans over a significant length of the continuous web. Also, any subsequent materials added to the defective portion of the web are often disposed of because of a lack of means to recapture those subsequent materials. Therefore, over a short period of time, the number of absorbent articles disposed of could add up to a significant amount.

Consequently, a need exists for an apparatus that reduces the downtime experienced by a production line caused by a defective portion of a continuous web. Also, a need exists for an apparatus which can minimize the impact of varying startup times on overall production. In addition, a need also exists for an apparatus that can reduce the number of finished products impacted by a part of the defective portion of a continuous web when the defective portion spans over a significant length of the continuous web.

SUMMARY OF THE INVENTION

An apparatus for decreasing downtime in a manufacturing process utilizing a continuous web as a raw material comprises a first transferring member, a second transferring member, and a storage member. The first transferring member is capable of carrying a continuous web from a first zone to a second zone at a first web speed. The second transferring member is positioned downstream of the first transferring member and is capable of carrying the continuous web from the second zone to a third zone at the first web speed. The storage member, which is downstream of the second transferring member, can store a contingent amount of the continuous web and can transfer the continuous web to a fourth zone at the first web speed.

The apparatus of the claimed invention further comprises a defect detection member, a first engaging member, and a second engaging member. The defect detection member is capable of detecting a defective portion in the continuous web in the first or second zones. The first engaging member is in communication with the defect detection member and is disposed adjacent to the second transferring member. The second transferring member is in communication with the defect detection member and is disposed between to the first transferring member and the second transferring member.

After the detection of the defective portion, the first engaging member engages the second transferring member thereby reducing the first web speed in the third zone to a second web speed. The second engaging member separates a part of the defective portion of the continuous web from non-defective portions of the continuous web thereby forming a first end and a second end. The second engaging member also splices the first end and the second end of the continuous web together. Pending the removal of the defective portion, the storage member provides a portion of the contingent amount of the continuous web to the fourth zone at the first web speed thereby reducing downtime and minimizing the number of defects in the finished products.

In another embodiment, the apparatus of the claimed invention may further comprise an upstream transferring member which supports the continuous web from a continuous web source to a first transferring member. The first transferring member may comprise an upper roll and a lower roll, wherein the upper and the lower rolls form a nip therebetween. Either the upper or lower rolls, or both can be driven such that the first transferring member transports the continuous web into the first zone.

The apparatus may further comprise a guide plate and an idler. The guide plate can be in contact with the surface of the lower roll, wherein the guide plate is fixed such that the continuous web is precluded from rotating around the surface of the lower roll. The idler, disposed downstream of the second transferring member, provides support for the continuous web in the third zone.

The defect detection member may comprise a camera and a central processing unit. The camera is capable of detecting a defective portion in the continuous web in the first zone and is disposed between the continuous web source and the upstream transferring member. The camera provides a visual image to a central processing unit for analysis. Both the first and second engaging members are in communication with the central processing unit such that after the detection of the defective portion, the central processing unit sends a signal to the first engaging member and the second engaging member to perform as described above.

A method for decreasing downtime in an absorbent article production line which utilizes a continuous web as a raw material comprises multiple steps. A continuous web is provided to the first zone at the first web speed. The first transferring member transports the continuous web from the first zone to the second zone at the first web speed. The second transferring member carries the continuous web from the second zone to the third zone at the first web speed. The storage member stores the contingent amount of continuous web and provides the continuous web to downstream processes.

The defect detection member inspects the continuous web in the first zone for a defective portion. The defect detection member is in communication with the first engaging member and the second engaging member. After the detection of a defective portion, the first engaging member is automatically engaged such that the continuous web is stopped at the second transferring member. In addition, after the detection of a defect, the second engaging member is automatically engaged such that the defective portion of the continuous web is separated from non-defective portions of the continuous web and the non-defective portions of the continuous web are attached. After the non-defective portions of the continuous web are attached together, the first engaging member is automatically disengaged such that the continuous web can be carried to the third zone at the first web speed or greater.

DETAILED DESCRIPTION OF THE INVENTION

Definitions:

As used herein, the following terms have the following meanings.

The term "attached" refers to elements being connected or united by fastening, adhering, bonding, etc. by any method suitable for the elements being attached together and their constituent materials. Many suitable methods for attaching elements together are well-known, including adhesive bonding, pressure bonding, thermal bonding, mechanical fastening, etc. Such attachment methods may be used to attach elements together over a particular area either continuously or intermittently.

The term "defect" is used herein to describe a visual or a physical flaw in the web or a laminated structure outside the range deemed acceptable by the manufacturer of the web or the laminated structure.

An "elastic," "elastomer", or "elastomeric", refers to polymers exhibiting elastic properties. They include any material that upon application of a force to its relaxed, initial length can stretch or elongate to an elongated length more than 10% greater than its initial length and will substantially recover back to about its initial length upon release of the applied force.

The term "extrude" or "extruding" refers herein to a process by which a heated elastomer is forced through one or more extrusion dies to form a molten stream of elastic that cools into a solid.

The term "nonwoven" refers herein to a material made from continuous (long) filaments (fibers) and/or discontinuous (short) filaments (fibers) by processes such as spunbonding, meltblowing, and the like. Nonwovens do not have a woven or knitted filament pattern.

The term "production line" is used herein to describe an overall process for converting a continuous web when assembled along with other materials, into a finished article. The "production line" may include converting operations (defined below) as well as other processes. The "production line" does not include a process of roll winding the continuous web for later processing.

The term "converting operation" is used herein to describe a stage or process in an absorbent article production line which manipulates the continuous web to form a laminated structure or a component of a disposable absorbent article such as an elastic waist band, an elastic cuff, or an elastic side panel.

The term "offline operation" is used herein to refer to a process or stage which is not directly included in the processes or stages of an absorbent article production line.

Description:

While an apparatus constructed in accordance with the claimed invention may be used in the offline operations of the continuous web, the apparatus offers several benefits when incorporated into the production line. For example, the apparatus of the present invention can reduce the downtime of production line by utilizing a contingent amount of the continuous web when a defective portion of the continuous web is detected. Another benefit is that the apparatus of the present invention can also reduce the number of finished products affected by the defective portion of the continuous web. Yet another benefit is that the apparatus can minimize the impact of the varying start up times of the various stages in the production line.

Figure 1:
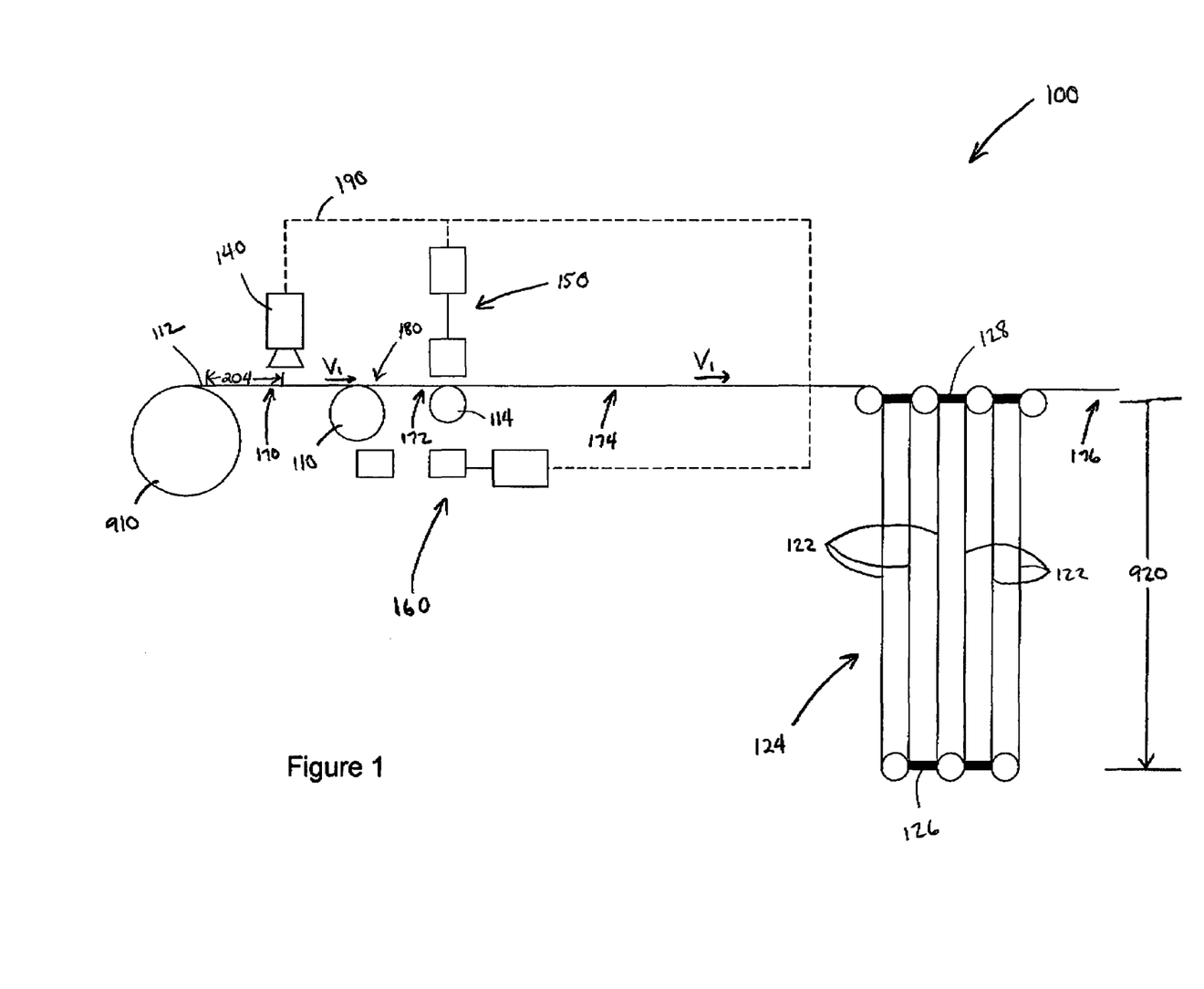
FIG. 1 is a schematic view of an apparatus constructed in accordance of the claimed invention.

As shown in FIG. 1, an apparatus 100 of the present invention may comprise a first transferring member 110, a second transferring member 114, and a storage member 124. A continuous web 112 can be fed from a web source 910 to the first transferring member 110 through a first zone 170 at a first web speed $V_1$. The first transferring member 110 can carry the continuous web 112 from the first zone to a second zone 172. The second transferring member 114 can carry the continuous web 112 from the second zone 172 to a third zone 174 at the first web speed $V_1$.

The storage member 124 is disposed downstream of the second transferring member 114. The storage member 124 can receive the continuous web 112 at the first web speed $V_1$ and can provide the continuous web 112 to a fourth zone 176 at the first web speed $V_1$ or a different web speed. In addition, the storage member 124 can store a contingent amount 122 of the continuous web, which can be provided to the fourth zone 176 in the event of the reduction of the first web speed $V_1$. Note that any converting operation known in the art may be included in the fourth zone 176.

The storage member 124 may comprise a translational carriage 126 and a stationary carriage 128. The contingent amount 122 is a portion of the continuous web 112 which travels between the translational carriage 126 and the stationary carriage 128. The storage member 124 provides the contingent amount 122 to the downstream processes pending the elimination of a defective portion 204 of the continuous web 112. During normal operation the translational carriage 126 can be stationary relative to the stationary carriage 128. During normal operation, the translatable carriage 126 can be in a full capacity position 920 which stores a maximum contingent amount 122 of the continuous web 112.

The translational carriage 126 may be arranged with an array of rolls which are upwardly movable. The stationary carriage 128 may be arranged with an array of fixed mounted rolls. The upwardly movable rolls can be coupled so as to move up and down as a unit when accumulating the contingent amount 122 or playing out a portion of the contingent amount 122 of the continuous web to the fourth zone 176. Alternatively, the upward movable rolls can move independently of one another.

The apparatus 100 further comprises a defect detection member 140 which is in communication 190 with a first engaging member 150 and a second engaging member 160. During normal operation, the defect detection member 140 inspects the continuous web 112 for defects as the continuous web 112 travels through the first zone 170. Note that the defect detection member 140 can inspect the web 112 for defects in the second zone 172 in conjunction with or independently from the first zone 170.

The first engaging member 150 can be disposed adjacent to the second transferring member 114. Upon the detection of a defective portion 204, the first engaging member 150 can engage the second transferring member 114, such that the first web speed $V_1$ of the continuous web 112 is reduced to a second web speed $V_2$. For example, the engaging member 150 can engage the second transferring member 114 such that the second web speed is zero. The amount of force required to reduce the first web speed will depend upon the material of the continuous web 112, the speed of the continuous web, and a number of other factors. Note that the first engaging member 150 should stop the continuous web 112 at the second transferring member 114 until the defective portion sags into the open area (see FIG. 2, item 168).

The second engaging member 160 can be disposed between the first transferring member 110 and the second transferring member 114. The second engaging member 160 can cut a part of the defective portion 204 from non-defective portions 180 of the continuous web 112. In addition, the second engaging member 160 can join non-defective portions 180 of the continuous web 112 together.

Figure 2:
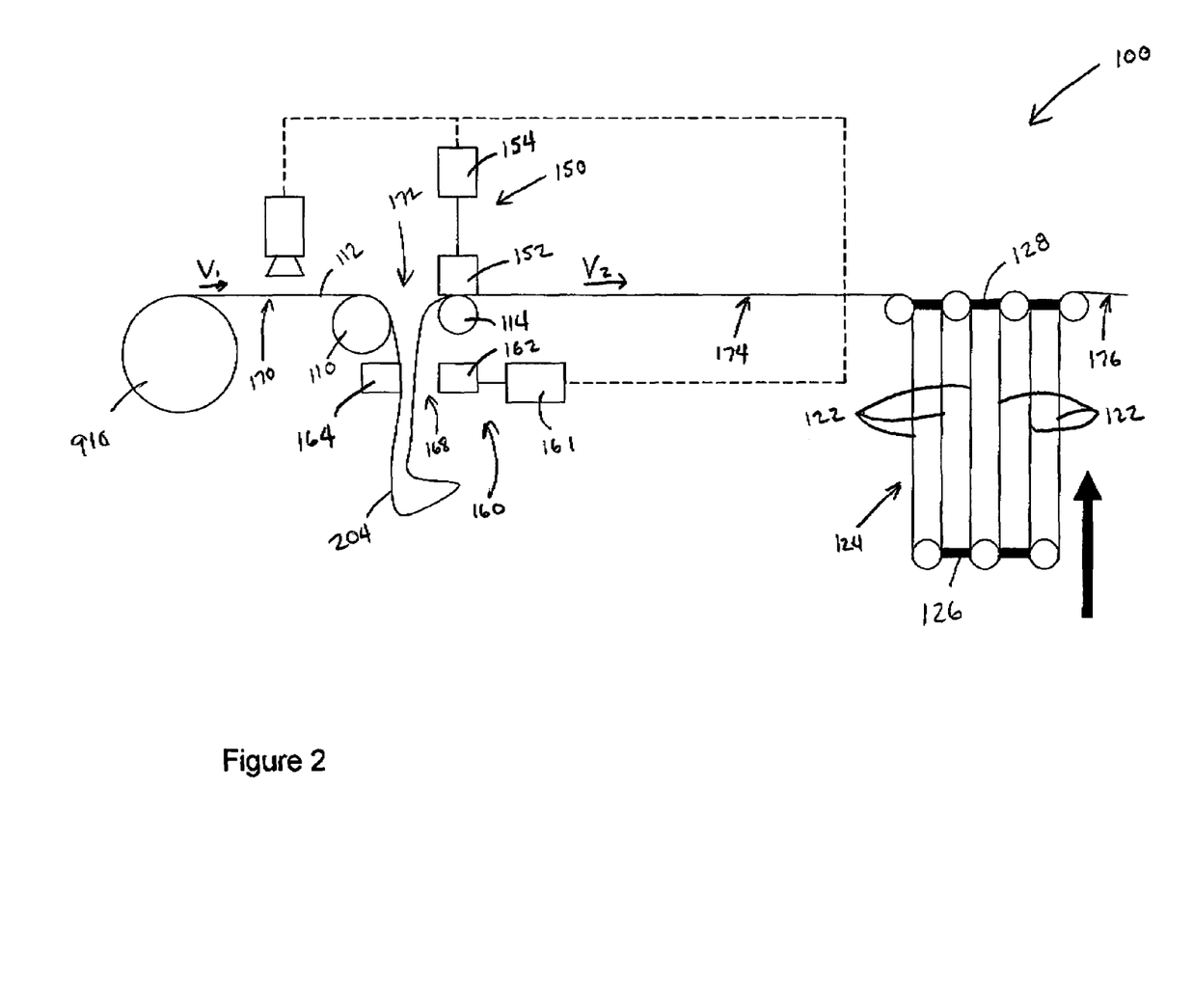
FIG. 2 is a schematic view of the apparatus of FIG. 1 showing the stopping or slowing of a continuous web by a first engaging member.

As shown in FIG. 2, the first engaging member 150 may comprise a braking element 152 which engages the second transferring member 114, and a first actuation element 154. The first actuation element 154 causes the braking element 152 to engage the second transferring member 114 upon the detection of the defective portion 204 or at some discrete time period thereafter. As discussed previously, in one embodiment, the braking element 152 can engage the second transferring member 114 such that $V_2$ is equal to zero.

The braking element 152 disclosed herein may comprise any device known in the art for stopping or reducing the speed of continuous webs. In one embodiment, the braking element 152 comprises a roller which is capable of engaging the second transferring member 114. If the braking element comprises a roller which is capable of engaging the second transferring member 114, the roller must be able to slow or completely stop the continuous web 112 carried by the second transferring member 114.

The second engaging member 160 may comprise a second actuation element 161, a cutting element 162, and a nip 164. The second actuation element 161 is capable of causing engagement between the cutting element 162 and the nip 164 upon the detection of the defective portion 204 or at some discrete time period thereafter.

As discussed previously, when the braking member 152 engages the second transferring member 114, the first web speed is reduced to a second web speed $V_2$ downstream of the second transferring member 114. However, the web source 910 can still provide the continuous web 112 at the first web speed $V_1$ upstream of the second transferring member 114. By providing the continuous web 112 upstream of the second transferring member 114, the defective portion 204 of the continuous web 112 sags into an open area 168 which is defined by the cutting element 162 and the nip 164.

Note that in order to ensure that the defective portion 204 sags into the open area 168, a web support means may be incorporated in the first zone such that the continuous web does not sag between the web source 910 and the first transferring member 110. Any means for supporting a web known in the art can be used. In another embodiment, the first transferring member 110 may be driven and can be equipped with a vacuum component such that the first transferring member 110 transports the continuous web 112 onto its circumference and transports the continuous web 112 from the first zone 170 into the second zone 172. The vacuum component should minimize slippage of the continuous web 112 with respect to the first transferring member's circumference. In yet another embodiment the first transferring member 110 may comprise a plurality of driven rolls which form a nip therebetween (see FIG. 5). In yet another embodiment, the first transferring member 110 may comprise a plurality of rolls which form an S-wrap configuration, wherein at least one of the plurality of rolls is driven.

As discussed previously, the first engaging member 150 slows or stops the continuous web 112 downstream of the second transferring member 114. Because the first engaging member 150 reduces the first web speed downstream of the second transferring member 114 in the third zone 174, the downstream processes in the fourth zone 176 utilize the contingent amount 122 of the continuous web 112 from the storage element 124. For example, when $V_2$ is equal to zero or is less than $V_1$, the translatable carriage 126 can move toward the stationary carriage 128 away from the full capacity position 920 (see FIG. 1). The movement of the translatable carriage 126 at the first web speed $V_1$ can allow any downstream processes to acquire the continuous web 112 at the first web speed $V_1$. Thus, even when the continuous web 112 is stopped in the first zone 170 or the second zone 172, the storage member 124 allows the downstream processes to receive the contingent amount 122 of the continuous web 112 and therefore keep running. By providing the contingent amount 122 of the continuous web 112 to the fourth zone 176, the apparatus 100 of the present invention reduces the downtime of the process when a defect in the continuous web 112 occurs.

Also, as discussed previously, another advantage of the claimed invention is that the impact of varying startup times on overall production can be minimized. For example, by providing the contingent amount 122 of the continuous web 112 to the downstream processes, the impact of a lengthy startup time for an upstream process can be eliminated. For example, if a process upstream of the apparatus 100 has a lengthy startup time, the contingent amount 122 of continuous web 112 can be fed to the downstream processes during the startup period of the upstream process thereby reducing the downtime of overall production.

Figure 3A:
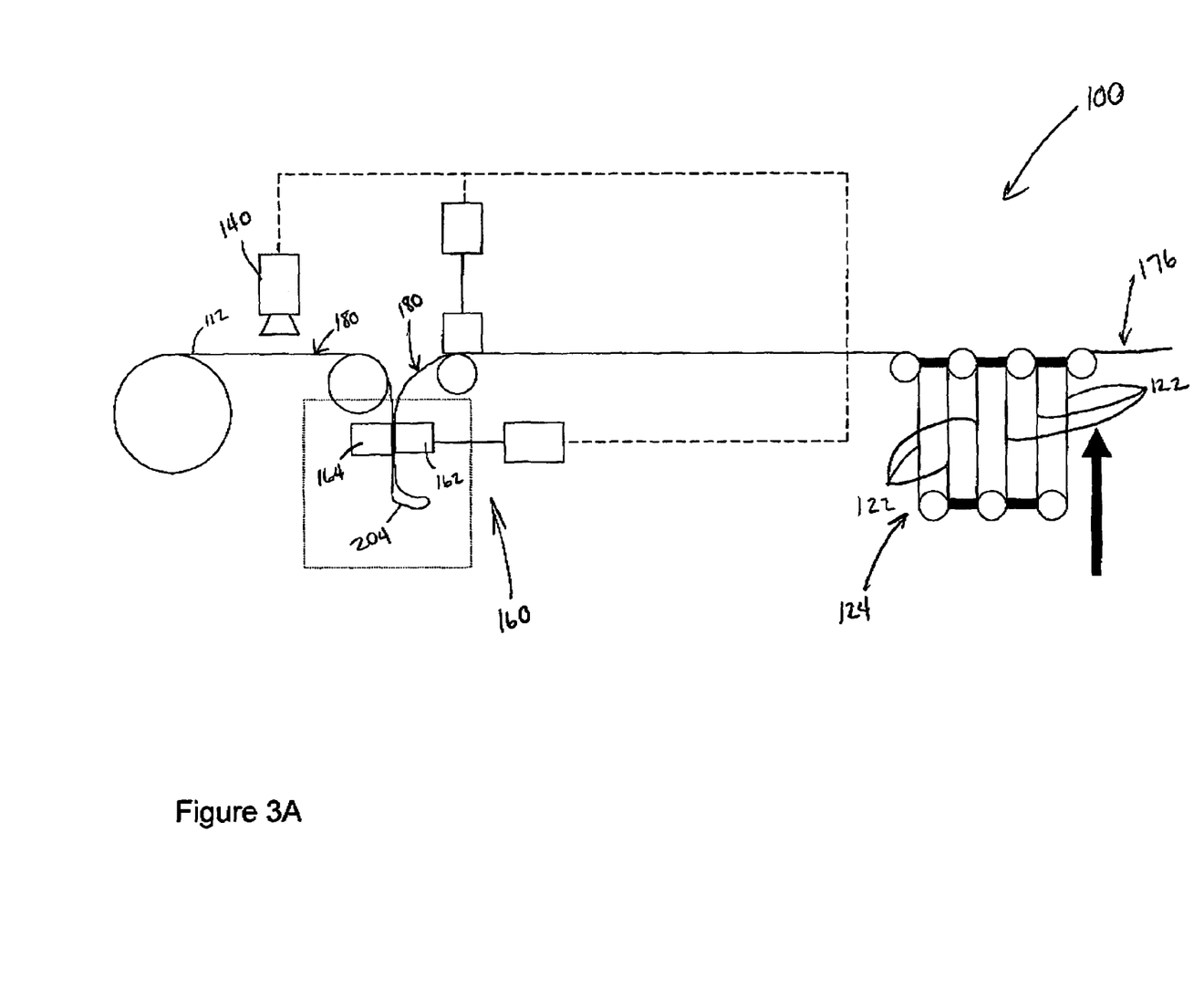
FIG. 3A is a schematic view of the apparatus of FIG. 1 showing the separation of a defective portion of the continuous web and the attaching of non-defective portion of the continuous web via a second engaging member.

As shown in FIG. 3A, the detection of a non-defective portion 180 of the continuous web 112 by the defect detection member 140 can cause the cutting member 162 to engage the nip 164 thereby separating the defective portion 204 of the continuous web 112 from non-defective portions 180 of the continuous web 112. Communication between the defect detection member 140 and the second engaging member 160 should be configured such that a majority of the defective portion 204 is completely cut away from the non-defective portions 180 of the continuous web 112. For example, assuming a first web speed of 5 m/s and the detection of the beginning of the defective portion (see FIG. 3B, item 224) at a position 10 m from the second engaging member 160, and a length of the defective portion of 5 m, the defect detection member 140 could send a signal to the second engaging member 160 after a delay of about 3 seconds. This could provide adequate time for the defective portion 204 of the continuous web 112 to sag in the open area 168 (see FIG. 2) and thereby be separated from the non-defective portions 180 of the continuous web 112.

Note that the removal of a part of the defective portion 204 may include the entire defective portion 204 or only a piece of the defective portion 204. In some instances the defective portion 204 of the continuous web 112 may be larger than the available contingent amount 122. If so, then the contingent amount 122 available to the fourth zone 176 will not be adequate for a complete removal of the defective portion 204 of the continuous web 112. Based on statistical data available to an operator, one skilled in the art could size the storage member 124 such that the available contingent amount 122 is larger than the defective portion 204 of the continuous web 112 in most instances. However, if an occasion occurs where the defective portion 204 is larger than the contingent amount 122 of the continuous web, there are some options available. The downstream processes in the fourth zone 176 can be stopped because of the lack of availability of the continuous web 112. Alternatively, a part of the defective portion 204 of the continuous web 112 can be removed rather than the entire defective portion 204. While, a number of finished products will be affected by the remaining defective portion, the number of finished articles impacted will be reduced because of the removal of the part of the defective portion 204. Another alternative is to slow the downstream processes down such that the contingent amount 122 of the continuous web 112 is used at a lower rate than normal.

Figure 3B:
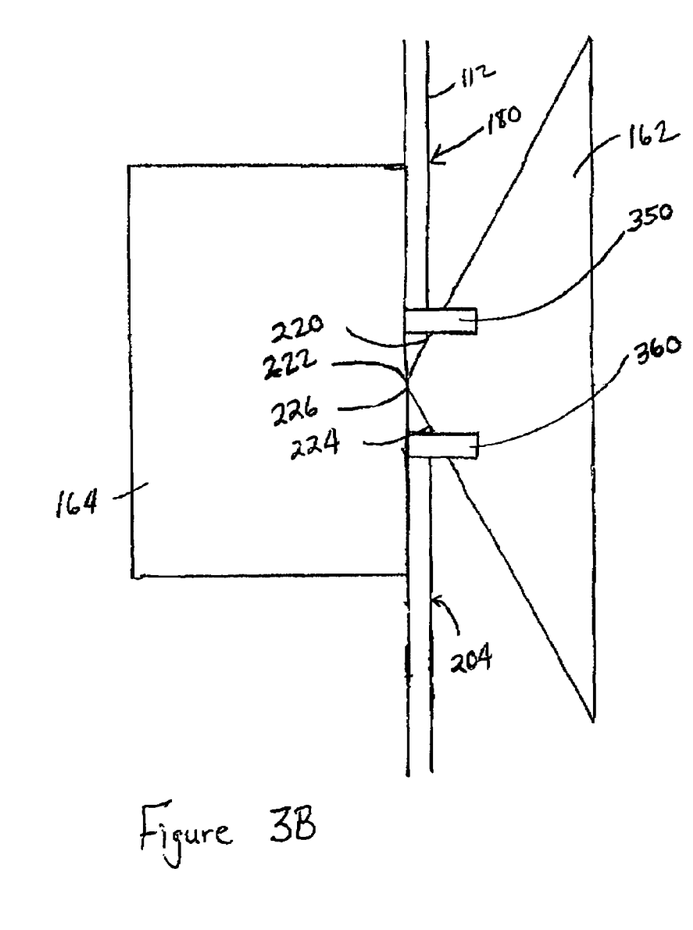
FIG. 3B is a close up view of a cutting element and a nip of the second engaging member of FIG. 3A.

As shown in FIG. 3B, the cutting element 162 may comprise a first bonding site 350. The first bonding site 350 can engage the nip 164 and the continuous web 112 proximate to a first end 220 and a second end 222 thereby attaching the non-defective portions 180 of the continuous web 112 together proximate to the first end 220 and the second end 222. The bond (butt splice, see FIG. 4, item 410) created by the first bonding site 350 creates a second defective portion (see FIG. 4, item 404) of the continuous web 112 which is smaller than the defective portion 204.

Optionally, the cutting element 162 may further comprise a second bonding site 360. The second bonding site 360 can engage the nip 164 and the continuous web 112 proximate to the third end 224 and a fourth end 226 thereby attaching the continuous web 112 together proximate to the third and fourth ends 224, 226. The second bonding site 360 creates a defective portion 204 of a web which is attached to itself proximate its third and fourth ends 224, 226.

In one embodiment, the first bonding site 350 and the second bonding site 360 apply pressure adjacent to the ends of the continuous web as described above creating a pressure bond. In another embodiment, an adhesive source may be incorporated such that adhesive bonds are created when the first bonding site 350 engages the nip 164. In yet another embodiment, at least the first bonding site 350 is heated such that a thermal bond adjacent to the first end 220 and the second end 222 is formed when the first bonding site 350 engages the nip 164.

If the first bonding site 350 is heated, then a wide range of temperatures can be used such that a thermal bond is created. The type of web to be bonded and the time allowed to create the thermal bond are just some of the factors which will determine the required temperature of the first bonding site 350. One skilled in the art could select a proper temperature for attaching the continuous web 112 to itself.

The cutting element 162 may comprise any device known in the art for cutting or separating continuous webs. The first bonding site and the second bonding site may comprise any device known in the art for attaching a continuous web.

Figure 4:
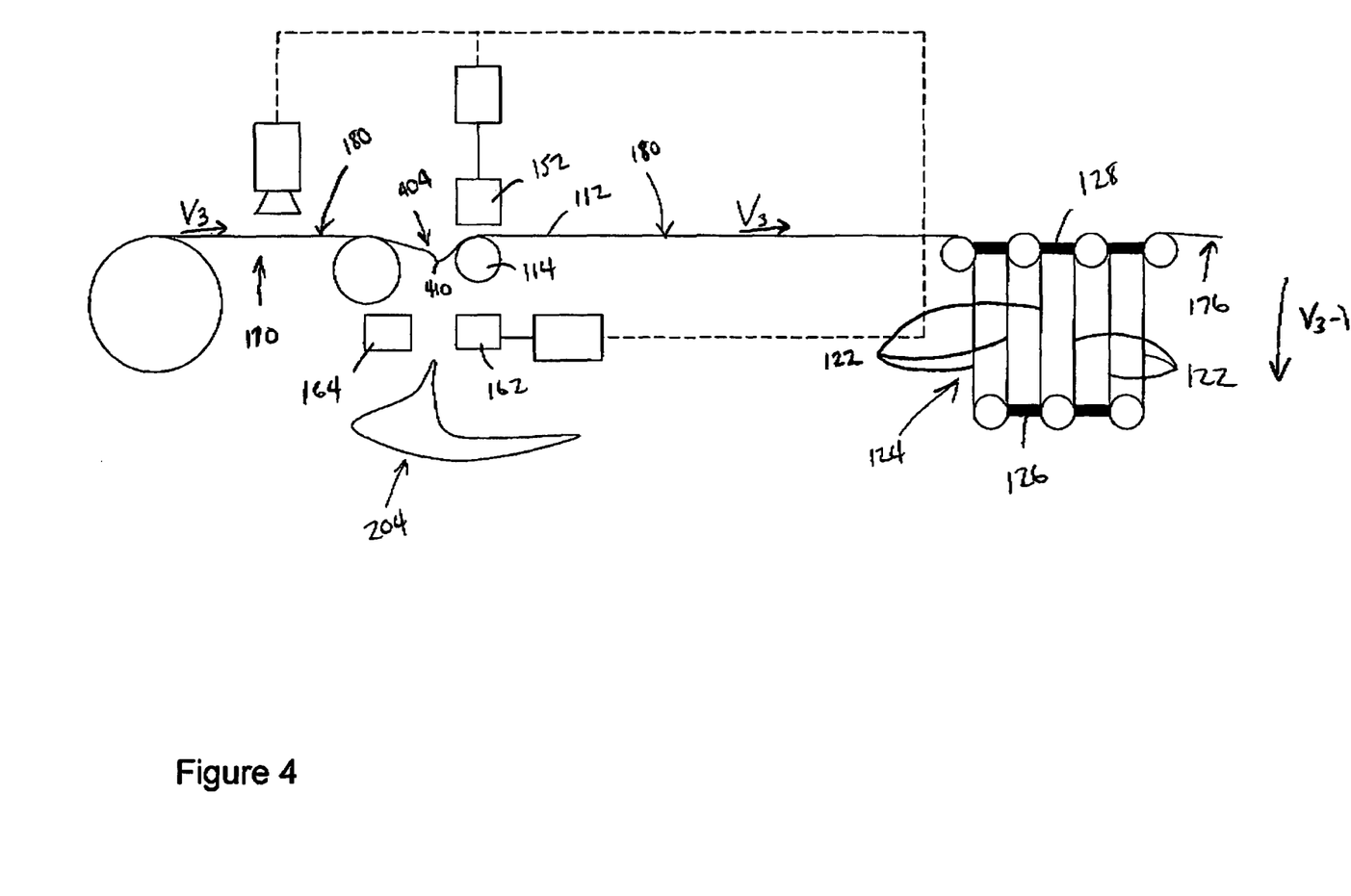
FIG. 4 is a schematic view of the apparatus of FIG. 1 showing the resumption of normal operation after the attaching of the non-defective portions of the continuous web.

As shown in FIG. 4, once the defective portion 204 of the web has been cut from the remainder of the continuous web 112, the cutting element 162 can disengage the nip 164. Similarly, the braking element 152 can disengage the second transferring member 114. Because the braking element 152 disengages the second transferring member 114, the second web speed $V_2$ can be increased such that it equals the first web speed $V_1$. Note however, that if the continuous web 112 is provided to the first zone 170 at the first web speed $V_1$ and the continuous web 112 is provided to the fourth zone 176 at the first web speed $V_1$, the storage member 124 will remain in a position of less than full capacity.

The speed of the continuous web 112 into the first zone 170 can be increased to a third web speed $V_3$ which is greater than the first web speed $V_1$. In addition, the continuous web 112 supplied to the storage member 124 can also be at the third web speed $V_3$. Consequently, the storage member 124 can regain the full contingent amount 122 of the continuous web 112. As an example, if $V_3$ is 8 m/s and $V_1$ is 5 m/s, then the translational carriage 126 can translate away from the stationary carriage 128 at a speed that is equal to about $V_3$-$V_1$ or 3 m/s.

Once the translational carriage 126 of the storage member 124 reaches its position of full capacity 920 (see FIG. 1), the translational carriage 126 can be stationary relative to the stationary carriage 128. In addition, when the translational carriage 126 is at its position of full capacity, the third web speed $V_3$ can be reduced to the first web speed $V_1$.

Note, as discussed previously, the butt splice 410 created by the first bonding site (see item 350 in FIG. 3B) is a defect in the continuous web 112. However, the second defective portion 404 of the continuous web 112 caused by the butt-splice 410 should be smaller than the defective portion 204 which was removed. Therefore, a smaller number of finished products will be impacted by the second defective portion 404 as opposed to the defective portion 204. Therefore, by separating the defective portion 204 from the non-defective portions 180 of the continuous web 112, the apparatus of the present invention reduces the number of finished products affected by the defect.

As discussed previously, the first transferring member may comprise a vacuum component which transports the continuous web onto the circumference of the first transferring member. In addition, in order to ensure that the defective portion of the continuous web sags into the open area, a portion of the first transferring member may be driven such that the defective portion of the continuous web is pushed into the open area. Also, as stated previously, in one embodiment, the first transferring member may comprise a pair of driven rolls (see FIG. 5).

Figure 5:
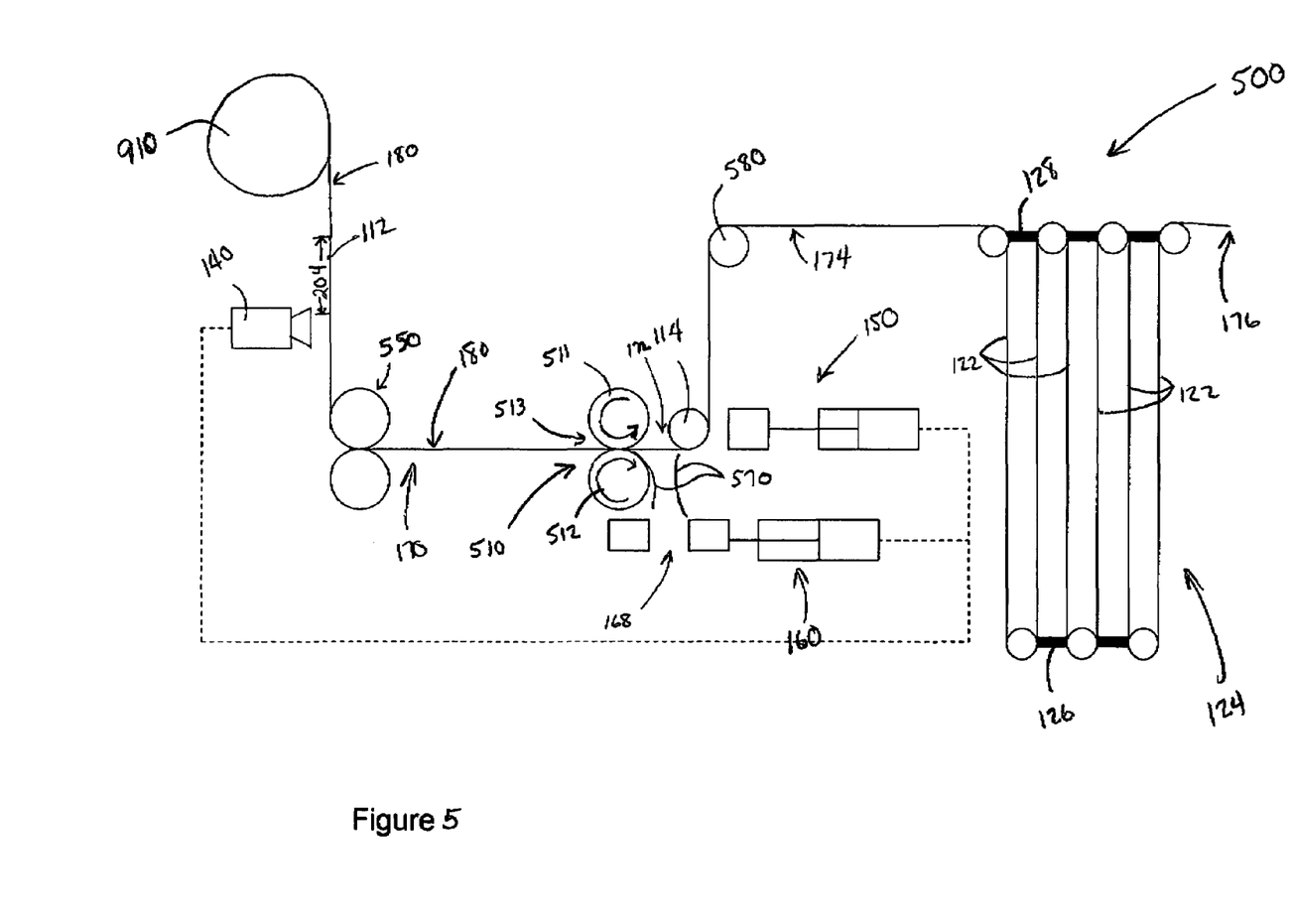
FIG. 5 is a schematic view of another embodiment of an apparatus constructed in accordance with the claimed invention.

As shown in FIG. 5, an apparatus 500 may comprise an upstream transferring member 550 which comprises a pair of rollers or a single roller. The upstream transferring member 550 can provide support for the continuous web 112 in the first zone 170. The upstream transferring member 550 can carry the continuous web 112 in the first zone 170 and provide the continuous web 112 to the first transferring member 510.

The apparatus 500 further comprises a first transferring member 510, the second transferring member 114, and the storage member 124. The first transferring member 510 includes a first roll 511 and a second roll 512. A second nip 513 is formed in between the first roll 511 and the second roll 512. The first roll 511, the second roll 512, or both, can be driven to ensure that the defective portion 204 of continuous web 112 is pushed into the open area 168.

The second transferring member 114 carries the continuous web 112 from the second zone 172 to the third zone 174. The storage member 124 is disposed downstream of the second transferring member 114 and operates as discussed with regard to the apparatus 100 (see FIG. 1). Optionally, the apparatus 500 may further comprise an idler 580 which also supports the continuous web 112 between the second transferring member 114 and the storage member 124.

Operating similar to the apparatus 100 (see FIG. 1), apparatus 500 comprises the defect detection member 140 which detects the defective portion 204 of the continuous web 112. At some discrete time interval after the detection of the defective portion, the first engaging member 150 can engage the second transferring member 114, such that the first web speed $V_1$ of the continuous web 112 is reduced to a second web speed $V_2$ in the third zone 174.

After the detection of the defective portion 204 of the continuous web 112, the first roll 511 and the second roll 512 can keep transporting the continuous web 112 into the first zone 170 at the first web speed $V_1$. Because the first roll 511 and second roll 512 transport the continuous web 112 at the first web velocity $V_1$ and because the continuous web 112 is slowed down or stopped at the second transferring member 114, the continuous web 112 in the second zone 172 sags into the open area 168. However, note that prematurely stopping the continuous web 112 could cause an excess of the non-defective portions 180 of the continuous web 112 to sag into the open area 168.

As discussed previously with regard to the apparatus 100 (see FIG. 1), the second engaging member 160 can cut the defective portion 204 from non-defective portions 180 of the continuous web 112. In addition, the second engaging member 160 can attach non-defective portions 180 of the continuous web 112 together.

In order to line up the continuous web 112 such that the defective portion 204 is separated from the non-defective portions 180 of the continuous web 112, the first roll 511 and the second roll 512 can reduce the speed of the continuous web. By reducing the speed of the continuous web 112 going into the open area 168, the second engaging member 160 may be able to more precisely separate the defective portion from the non-defective portion.

Optionally, the apparatus 100 (see FIG. 1) of the apparatus 500 may further comprise guide plates 570. The guide plates 570 can be disposed adjacent to the surface of the first transferring member 510 and adjacent the surface of the second transferring member 114. The guide plates 570 can guide the defective portion 204 of the continuous web 112 into the open area 168. Also, the guide plate 570 can preclude the continuous web 112 from wrapping around the first transferring member 510, the second transferring member 114, or any components thereof.

The defect detection member may comprise any means of defect detection known in the art. The defect detection member may comprise a visual element. In one embodiment, the visual element comprises a human detection element which subsequently utilizes the first and second engaging members to remove the defective portion of the continuous web. A suitable visual element is any device known in the art for visually inspecting a continuous web or laminated structure. In one embodiment, the visual element comprises a digital camera.

The defect detection member may communicate with the engaging members in a number of different manners. For example, instead of supplying a signal to the first engaging member and the second engaging member, the defect detection member may alternatively provide an indication of a defect or a defective portion by signaling an operator. The operator may then intervene and utilize both the first engaging member and the second engaging member to remove the defective portion of the continuous web.

While there is no requirement that the first and second engaging member react automatically, they can be configured to do so. In one embodiment, the defect detection member, after detecting a defect, coordinates signals to both the first engaging member and the second engaging member, without operator intervention, such that the defect is removed without interrupting the upstream or downstream processes. In another embodiment, the defect detection member comprises a camera, e.g. a digital camera, which transmits a visual image signal to a central processing unit. After analyzing the visual image signal, the central processing unit can create or not create a signal to the first and second engaging members based on the analysis. For embodiments utilizing the central processing unit, a suitable software program for analyzing data input into from the digital camera is sold under the trade name DT Vision Foundry™ 3.6 by Data Translations Inc.™ in Marlboro, Mass.

A web may contain many abnormalities which are considered to be defects which cause defective portions of the continuous web. For instance, a hole having a diameter above a certain threshold or perhaps a discoloration may constitute a defect in a continuous web. As another example, in a laminated continuous web comprising a substrate and a plurality of elastomeric strands, a broken or missing strand may constitute a defect.

Figure 6A:
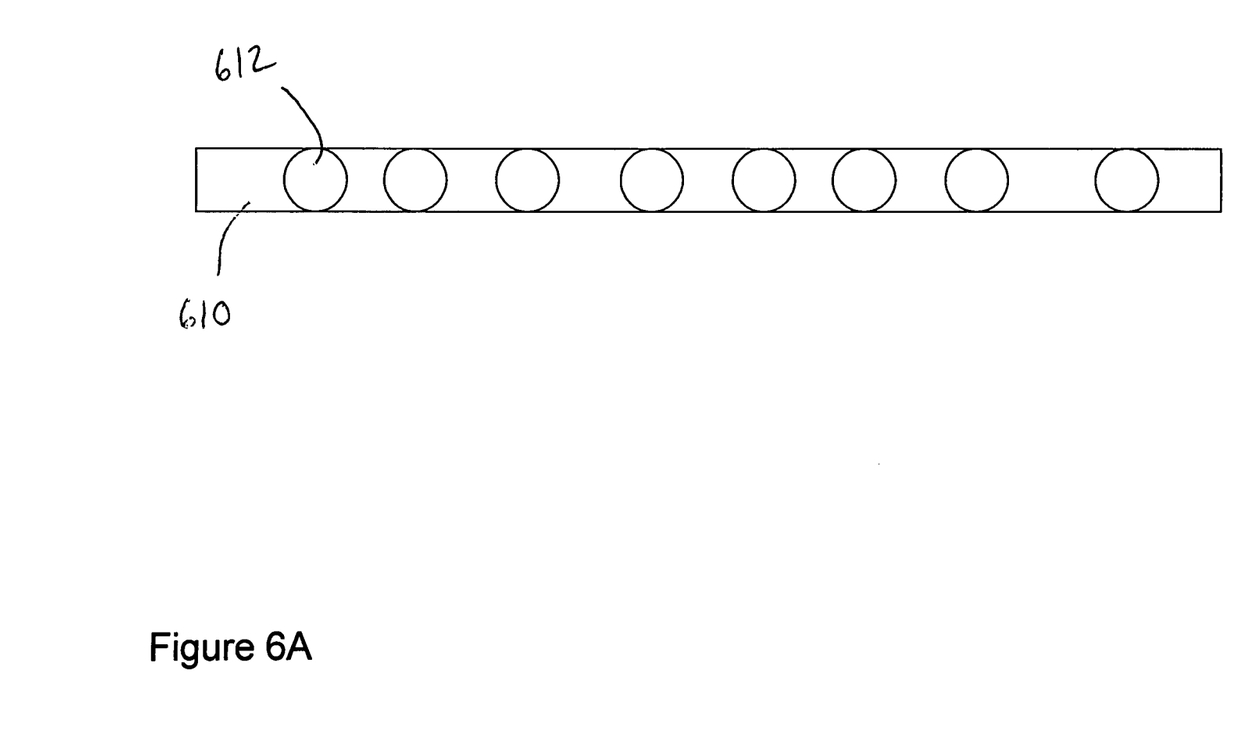
FIGS. 6A and 6B show visual image examples which constitute a defect in a continuous web.
Figure 6B:
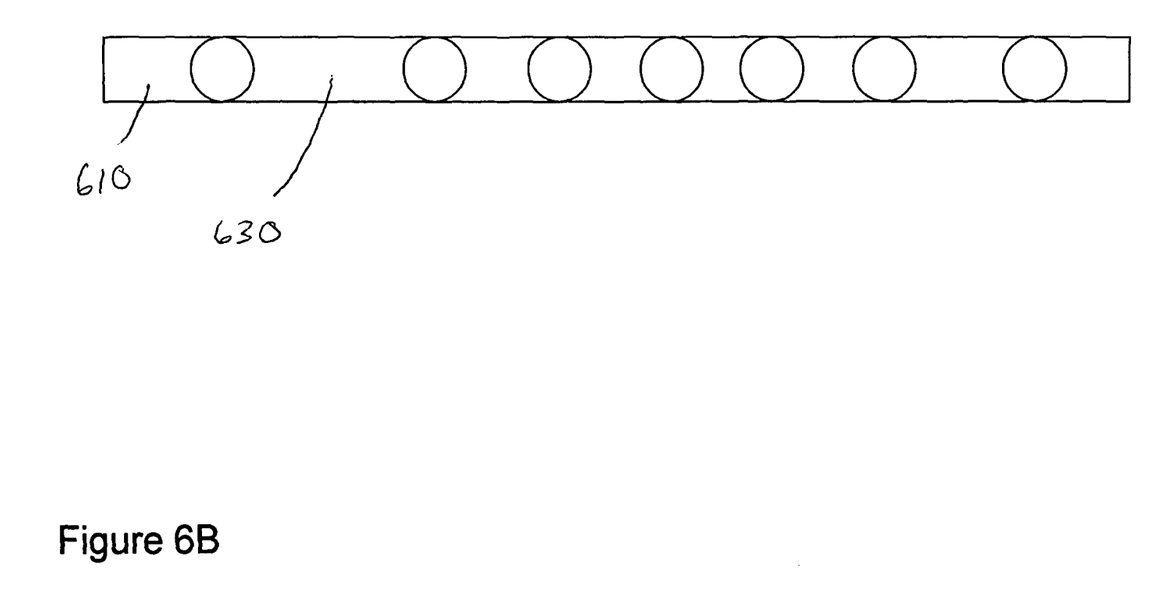

FIGS. 6A-6B provide an example of images that can be inspected by the visual element. As shown in FIG. 6A, a laminate web 610 including a plurality of elastomeric strands 612 can be inspected by the visual element. A total of eight elastomeric strands are shown. As shown in FIG. 6B, a defect occurs when at least one elastomeric strand 630 is not present in the laminate web 610. As discussed previously, upon the detection of a defect, the defect detection member can provide a signal to the first engaging member and the second engaging member.

The continuous web may comprise any nonwoven, woven, or combination thereof. The continuous web may comprise any material known in the art. The continuous web may comprise fibers made of polypropylene, polyethylene, polyester, nylon, cellulose, polyamide, or combinations of such materials. Fibers of one material or fibers of different materials or material combinations may be used in the continuous web.

A nonwoven web can be made by any process known in the art. Exemplary processes include spunbond, spunbond meltblown spunbond (SMS), spunbond meltblown meltblown spunbond (SMMS), carded and the like. Particularly acceptable nonwovens include high elongation carded (HEC) nonwovens and deep activation polypropylene (DAPP) nonwovens.

The nonwoven web may comprise fibers that are bonded internally, including fibers that are needle punched, hydro entangled, spun bonded, thermally bonded, bonded by various types of chemical bonding such as latex bonding, powder bonding, and the like.

The continuous web may further comprise an elastomeric layer. The elastomeric layer may comprise a plurality of elastomeric strands which extend in a parallel uniformly spaced arrangement on the web. However, the elastomeric strands may be arranged in any configuration desired. For instance, the strands may be arranged to provide a specific force profile in the elastomeric nonwoven laminate by varying the thickness of the individual strands or the spacing between them.

In addition, the shape of the elastomeric strands is not limited. For example, typical elastomeric strands have a circular cross sectional shape, but sometimes the plurality of elastomeric strands may have different shapes, such as a trilobal shape, or a flat (i.e., "ribbon" like) shape. Further, the thickness or diameter of the elastomeric strands may vary in order to accommodate a particular application.

The plurality of elastomeric strands is preferably made of a resiliently elastic thermoplastic material. The elastomeric strands may be made from liquid elastomeric that can be extruded through a die to achieve a desired strand elastomeric diameter and/or shape. The elastomeric strands are preferably styrene block copolymers, polyurethane or latex rubber having a diameter ranging between about 0.15 mm and about 0.5 mm and a density ranging from about 600 kg/m$^3$ to about 1250 kg/m$^3$.

The web source described herein may comprise an upstream process excluding an unwind stand. Some suitable upstream processes are described further in the following cases: U.S. Ser. No. 10/452,438 and entitled "METHOD AND APPARATUS FOR PRODUCING ELASTOMERIC NONWOVEN LAMINATES" filed on Jun. 2, 2003 and U.S. Ser. No. 10/836,944 and entitled "APPARATUS FOR PRODUCING ELASTOMERIC NONWOVEN LAMINATES" filed on Apr. 30, 2004. In one embodiment, the web source is an upstream converting operation.

The transferring members disclosed herein, i.e. the first and the second, can be any device known in the art for carrying or transporting webs. The transferring devices may comprise rollers, bars, etc. Similarly, the first and second actuation elements can be any devices known in the art which cause engagement between two elements.

The storage member may comprise any device known in the art for storing web material. For example, the storage member may comprise a festoon, which is, by design, a low mass, low inertia device. The festoon can be biased so as to hold, at steady state operation, an accumulation of the continuous web equivalent to approximately half its capacity for web accumulation. Thus, starting from steady state, the festoon can either accumulate more of the continuous web if a downstream function is temporarily interrupted or can play out the accumulated length of web if an upstream function is temporarily interrupted.

Optionally, the festoon may be used to control tension in the continuous web. Further discussion about the control of tension in a continuous web can be found in U.S. Pat. No. 6,856,850 issued to Rajala et al.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for decreasing downtime in a manufacturing process utilizing a continuous web as a raw material, the apparatus comprising:
    a first transferring member comprising at least one roll capable of carrying a continuous web from a first zone to a second zone at a first web speed;
    a second transferring member downstream of the first transferring member, the second transferring member comprising at least one roll capable of carrying the continuous web from the second zone to a third zone at the first web speed;
    a storage member downstream of the second transferring member which can store a contingent amount of the continuous web and can transfer the continuous web to a fourth zone at the first web speed;
    a defect detection member capable of detecting a defective portion in the continuous web in the first or second zones;
    a first engaging member being disposed adjacent to the second transferring member and comprising a first actuation element and a braking element, wherein the first actuation element is adapted to engage the braking element with the at least one roll of the second transferring member; and
    a second engaging member being disposed between the first transferring member and the second transferring member, member, the second engaging member comprises a second actuation element, a cutting element, and a nip, wherein the second actuation element can cause the cutting element to engage the nip, wherein the cutting element further comprises a first bonding site which is capable of engaging the nip and the continuous web thereby attaching the continuous web proximate to a first end and a second end, wherein the first bonding site is heated such that a thermal bond is created in the continuous web; and
    a central processing unit in communication with the defect detection member, the first engaging member, and the second engaging member and the second engaging member in a sequence wherein after the detection of the defective portion:
    (a) the braking element engages the at least one roll of the second transferring member thereby reducing the first web speed in the third zone to a second web speed while the first transferring member continuously carries the continuous web form the first zone to the second zone at the first web speed and carries the defective portion from the first zone to the second zone at the first web speed; and (b) wherein the second engaging member reduces the defective portion by separating a part of the defective portion from the continuous web thereby forming a first end and a second end, wherein the second engaging member splices the first end and the second end of the continuous web together, and wherein the storage member provides a portion of the contingent amount of the continuous web to the fourth zone at the first web speed thereby reducing downtime and minimizing the number of defects in the finished products.

2. The apparatus of claim 1, wherein the cutting element and the nip define an open area which is capable of receiving the defective portion of the continuous web and non-defective portions of the continuous web.

3. The apparatus of claim 1, further comprising an adhesive source for applying adhesive to the continuous web such that an adhesive bond is formed when the first bonding site engages the continuous web and the nip.

4. The apparatus of claim 1, wherein the cutting element further comprises a second bonding site which is capable of engaging the nip and the defective portion of the continuous web thereby attaching the defective portion of the continuous web to itself.

5. The apparatus of claim 1, wherein the defect detection member comprises a visual element and a central processing unit, wherein the visual element is in signal communication with the central processing unit.

6. An apparatus for decreasing downtime in a manufacturing process utilizing a continuous web as a raw material, the apparatus comprising:
    an upstream transferring member which supports the continuous web from a continuous web source to a first transferring member;
    the first transferring member capable of carrying a continuous web from a first zone to a second zone at a first web speed, wherein the first transferring member comprises an upper roll and a lower roll, wherein the upper and the lower rolls form a nip therebetween, and wherein the upper and the lower rolls are driven such that the first transferring member transports the continuous web into the first zone;
    a guide plate in contact with the surface of the lower roll, wherein the guide plate is fixed such that the continuous web is precluded from rotating around the surface of the lower roll;
    a second transferring member downstream of the first transferring member, the second transferring member comprising at least one roll capable of carrying the continuous web from the second zone to a third zone at the first web speed;
    an idler downstream of the second transferring member supporting the continuous web in the third zone;
    a storage member downstream of the second transferring member which can store a contingent amount of the continuous web and can transfer the continuous web to a fourth zone at the first web speed;
    a camera capable of detecting a defective portion in the continuous web in the first zone, wherein the camera is disposed between the continuous web source and the upstream transferring member, wherein the camera provides a visual image;
    a first engaging member being disposed adjacent to the second transferring member and comprising a first actuation element and a braking element, wherein the first actuation element is adapted to engage the braking element with the at least one roll of the second transferring member; and a second engaging member being disposed between the first transferring member and the second transferring member, wherein the second engaging member comprises a second actuation element, a cutting element, and a nip, wherein the second actuation element can cause the cutting element to engage the nip, wherein the cutting element further comprises a first bonding site which is capable of engaging the nip and the continuous web thereby attaching the continuous web proximate to a first end a second end wherein the first bonding site is heated such that a thermal bond is created in the continuous web; and a central processing unit in communication with the camera, the first engaging member, and the second engaging member, the central processing unit configured to operate the first engaging member and second engaging member in a sequence wherein after the detection of the defective portion, (a) the central processing unit sends a signal to the first engaging member to engage the braking element with the at least one roll of the second transferring member thereby reducing the first web speed in the third zone to a second web speed while the first transferring member continuously carries the continuous web form the first zone to the second zone at the first web speed and carries the defective portion from the first zone to the second zone at the first web speed; and (b) wherein the central processing unit sends a signal to the second engaging member to separate a part of the defective portion from the continuous web, thereby forming a first end and a second end, wherein the second engaging member splices the first end and the second end of the continuous web together, and wherein the storage member provides a portion of the contingent amount of the continuous web to the fourth zone at the first web speed thereby reducing downtime and minimizing the number of defects in the finished products.

7. The apparatus of claim 6, wherein the cutting element and the nip define an open area which can receive the defective portion of the continuous web and non-defective portions of the continuous web.

8. The apparatus of claim 6, further comprising an adhesive source for applying adhesive to the continuous web such that an adhesive bond is formed when the first bonding site engages the continuous web and the nip.

9. The apparatus of claim 6, wherein the cutting element further comprises a second bonding site which is capable of engaging the nip and the defective portion of the continuous web thereby bonding the defective portion of the continuous web to itself.

10. The apparatus of claim 1, wherein the first transferring member comprises a first roll and a second roll, wherein the first and the second rolls form a nip therebetween, and wherein the first and the second rolls are driven such that the first transferring member transports the continuous web into the first zone.

* * * * *

UNITED STATES PATENT AND TRADEMARK OFFICE
CERTIFICATE OF CORRECTION

| | | |
|---|---|---|
| PATENT NO. | : 8,910,689 B2 | Page 1 of 1 |
| APPLICATION NO. | : 11/079963 | |
| DATED | : December 16, 2014 | |
| INVENTOR(S) | : Uwe Schneider | |

It is certified that error appears in the above-identified patent and that said Letters Patent is hereby corrected as shown below:

In the Claims

Column 12

Line 48, delete the second occasion of "member," and insert -- wherein --.

Signed and Sealed this
Seventh Day of April, 2015

Michelle K. Lee
*Director of the United States Patent and Trademark Office*